United States Patent
Bond et al.

(10) Patent No.: US 10,184,883 B2
(45) Date of Patent: Jan. 22, 2019

(54) DETECTING ISOTOPOLOGUES OF CARBON DIOXIDE IN THE ATMOSPHERE IN CONCOMITANCE OF WATER OR METHANE

(71) Applicant: LAWRENCE LIVERMORE NATIONAL SECURITY, LLC, Livermore, CA (US)

(72) Inventors: Tiziana C. Bond, Livermore, CA (US); Mihail Bora, Livermore, CA (US); Jessica L. Osuna, San Leandro, CA (US); Sonia Wharton, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 96 days.

(21) Appl. No.: 15/353,988

(22) Filed: Nov. 17, 2016

(65) Prior Publication Data

US 2018/0136113 A1    May 17, 2018

(51) Int. Cl.
| | |
|---|---|
| *G01N 21/01* | (2006.01) |
| *G01N 21/03* | (2006.01) |
| *G01N 21/39* | (2006.01) |
| *G01N 33/00* | (2006.01) |

(52) U.S. Cl.
CPC ............ *G01N 21/031* (2013.01); *G01N 21/39* (2013.01); *G01N 33/004* (2013.01); *G01N 2021/399* (2013.01); *G01N 2201/021* (2013.01)

(58) Field of Classification Search
CPC .................................................... G01N 21/031

USPC ........................................................ 356/437
See application file for complete search history.

(56) References Cited

U.S. PATENT DOCUMENTS

| | | | |
|---|---|---|---|
| 2010/0139644 A1* | 6/2010 | Schwarzbach | ............ F24J 2/07 126/573 |
| 2010/0198736 A1* | 8/2010 | Marino | .............. G01N 21/3504 705/308 |
| 2011/0164251 A1* | 7/2011 | Richter | ................ G01N 21/031 356/440 |

(Continued)

OTHER PUBLICATIONS

Bingham et al., "Development of a Miniature, Rapid Response Carbon Dioxide Sensor", Lawrence Livermore National Laboratory, 1978, 23 pp.

(Continued)

*Primary Examiner* — Tarifur Chowdhury
*Assistant Examiner* — Omar Nixon
(74) *Attorney, Agent, or Firm* — Eddie E. Scott

(57) ABSTRACT

A meteorological tower is provided in a flux site and a solar array is positioned on the tower to provide power. A laser on the tower receives power from the solar array and produces a laser beam. A multiplicity of individual laser absorption spectroscopy gas cells positioned on the meteorological tower collect samples of the atmosphere. An optical cable connects the laser to each of individual las cell and direct the laser beam into each cell. Each cell includes a multiplicity of mirrors positioned so that the laser beam makes a multiplicity of passes through the samples. An analyzer associated with the cells receives the laser beam after the laser beam has made the multiplicity of passes through the sample of the atmosphere and the analyzer detects concentrations of isotopes of carbon dioxide in the atmosphere in concomitance of other gas concentrations.

6 Claims, 5 Drawing Sheets

(56) References Cited

U.S. PATENT DOCUMENTS

2013/0050704 A1* 2/2013 Padilla Viquez ......... G01J 3/02 356/402

OTHER PUBLICATIONS

Bond et al., "Gas Spectroscopy Using Tunable Vertical Cavity Surface Emitting Lasers", Lawrence Livermore National Laboratory, 12, pp. 1-45.

Griffis, "Tracing the flow of carbon dioxide and water vapor between the biosphere and atmosphere: A review of optical isotope techniques and their application", Agricultural and Forest Meteorology 174-175, 2013, pp. 85-109.

Lai et al., "Canopy-scale delta 1(3)C of photosynthetic and respiratory CO2 fluxes: observations in forest biomes across the United States", Global Change Biology, 11(4), 2005, pp. 633-643.

Lai, "Estimating photosynthetic C-13 discrimination in terrestrial CO2 exchange from canopy to regional scales", Global Biogeochemical Cycles, vol. 18, 2004, pp. 1-11.

Lai et al., "Seasonal and interannual variations of carbon and oxygen isotopes of respired CO2 in a tallgrass prairie: Measurements and modeling results from 3 years with contrasting water availability", Journal of Geophysical Research—Atmospheres vol. 111, 2006, pp. 1-14.

Shim et al., "The role of interannual, seasonal, and synoptic climate on the carbon isotope ratio of ecosystem respiration at a semiarid woodland", Global Change Biology, 17, 2011, pp. 2584-2600.

Sturm et al., "Eddy covariance measurements of CO2 isotopologues with a quantum cascade laser absorption spectrometer", Agricultural and Forest Meteorology, 152, 2012, pp. 73-82.

Wharton et al., "Old-growth CO2 flux measurements reveal high sensitivity to climate anomalies across seasonal, annual and decadal time scales," Agricultural and Forest Meteorology, 161, 2012, pp. 1-14.

\* cited by examiner

DETECTING ISOTOPOLOGUES OF CARBON DIOXIDE IN THE ATMOSPHERE IN CONCOMITANCE OF WATER OR METHANE

STATEMENT AS TO RIGHTS TO APPLICATIONS MADE UNDER FEDERALLY SPONSORED RESEARCH AND DEVELOPMENT

The United States Government has rights in this application pursuant to Contract No. DE-AC52-07NA27344 between the United States Department of Energy and Lawrence Livermore National Security, LLC for the operation of Lawrence Livermore National Laboratory.

BACKGROUND

Field of Endeavor

The present application relates to detecting isotopologues of carbon dioxide in the atmosphere and more particularly to detecting isotopologues of carbon dioxide in the atmosphere in concomitance of water or methane in a flux site.

State of Technology

This section provides background information related to the present disclosure which is not necessarily prior art.

The flux community had its beginnings in the Harvard Forest. At its founding in 1907, the original purpose of the Harvard Forest was to serve as: a field laboratory for students, a research center in forestry and related disciplines, including soils, wildlife biology, geography and botany, and a demonstration of practical sustained forestry. In 1914, Forestry education was shifted to Petersham, and the Harvard Forest was made a graduate school. The Harvard Forest mission was reprioritized in 1915 to include serving as an example to the local community for the care and marketing of forests. In 1932, the Harvard Forest was placed within Harvard's Faculty of Arts and Sciences and Graduate School of Arts and Sciences, where it has remained since.

In 2012, the U.S. Department of Energy (DOE) established the AmeriFlux Management Project (AMP) at Lawrence Berkeley National Laboratory (LBNL) to support the broad AmeriFlux community and the AmeriFlux sites. AmeriFlux is now one of the DOE Office of Biological and Environmental Research's (BER) best-known and most highly regarded brands in climate and ecological research. AmeriFlux datasets, and the understanding derived from them, provide crucial linkages between terrestrial ecosystem processes and climate-relevant responses at landscape, regional, and continental scales.

The AmeriFlux network started with a group of ad hoc flux towers already operating in such locales as Harvard Forest in Massachusetts, Walker Branch Watershed in Tennessee, Howland Forest in Maine, and at the Camp Sherman site in Oregon. By 1999 new towers were established at Duke Forest loblolly pine plantation and deciduous forest in North Carolina, on the Wind River Crane in Washington, at Morgan Monroe State deciduous forest in Indiana, on Niwot Ridge in subalpine forest of Colorado, near Douglas Lake at the University of Michigan Biological Station, at agricultural sites in Oklahoma and Illinois, over a slash pine plantation in Florida, a grassland near Fort Peck, Mont., at a chaparral in southern California, and at a ponderosa pine plantation in northern California.

The flux community currently relies on commercially available infrared gas analyzer (IRGA) units to measure $CO_2$ and $H_2O$ concentrations (e.g., $[CO_2]$). In conjunction with sonic anemometers, $CO_2$ and $H_2O$ fluxes are also calculated with a technique called eddy covariance. The IRGAs measure $[CO_2]$ and $[H_2O]$ with a precision of approximately 0.15 µmol mol−1 and 0.006 mmol mol−1, respectively, at sampling frequencies of up to 50 Hz and consume up to 30 W of power, costing at least $20K for one basic unit. As such, most sites measure fluxes at only one location, usually above the canopy, and very few sites measure ecosystem-relevant isotopes of carbon and oxygen. Recent technological advances have shown that measurements of multiple $CO_2$ isotopologues ($12C16O_2$, $13C16O_2$, $18O_{12}C_{16}O$) have the potential to reveal key information about the partitioned (photosynthesis and respiration) fluxes. Originally, samples had to be collected in flasks and transported to a facility with an isotope ratio mass spectrometer (IRMS) for analysis. In the past decade, advances have made it possible to measure in situ but still require an air-conditioned shed and large amounts of power. Sampling frequency is on the order of 10 minutes or more, and instruments cost nearly $100K according to recent quotes received from the leading suppliers of isotope measurement instruments.

SUMMARY

Features and advantages of the disclosed apparatus, systems, and methods will become apparent from the following description. Applicant is providing this description, which includes drawings and examples of specific embodiments, to give a broad representation of the apparatus, systems, and methods. Various changes and modifications within the spirit and scope of the application will become apparent to those skilled in the art from this description and by practice of the apparatus, systems, and methods. The scope of the apparatus, systems, and methods is not intended to be limited to the particular forms disclosed and the application covers all modifications, equivalents, and alternatives falling within the spirit and scope of the apparatus, systems, and methods as defined by the claims.

The inventors' apparatus, systems, and methods are used in flux sites for detecting concentrations isotopes, specifically the various isotopologues of $CO_2$ in the atmosphere in concomitance of other gases concentration such $H_2O$ and $CH_4$. The inventors' apparatus, systems, and methods have use with the partitioned components (photosynthesis and respiration) of the net ecosystem exchange of $CO_2$ as well as their independent responses to environmental drivers in situ, with also increasing the spatial and temporal resolution of sampled carbon fluxes and isotopologues. Current technologies are inadequate for detecting the small changes necessary to detect these dynamic processes.

The inventors' apparatus, systems, and methods have use in flux sites for detecting concentrations of isotopes of carbon dioxide in the atmosphere in concomitance of other gas concentrations. In various embodiments the inventors' apparatus, systems, and methods include a meteorological tower in the flux site; a solar array positioned on the meteorological tower wherein the solar array produces power; a laser in the flux site positioned on the meteorological tower that receives the power from the solar array wherein the laser produces a laser beam; a multiplicity of individual laser absorption spectroscopy gas cells positioned on the meteorological tower wherein the multiplicity of individual laser absorption spectroscopy gas cells receive the power from the solar array and wherein the multiplicity of individual laser absorption spectroscopy gas cells receive a sample of the atmosphere; an optical cable connecting the laser to each of the individual laser absorption spectroscopy gas cells that directs the laser beam into each of the individual laser absorption spectroscopy gas cells, wherein each of the individual laser absorption spectroscopy gas cells includes a multiplicity of mirrors positioned inside of each of the individual laser absorption spectroscopy gas cells so that the laser beam makes a multiplicity of passes through the sample of the atmosphere inside of each of the individual laser absorption spectroscopy gas cells; and an analyzer associated with each the individual laser absorption spectroscopy gas cells wherein the analyzer receives the laser beam after the laser beam has made the multiplicity of passes through the sample of the atmosphere and the analyzer detects concentrations of isotopes of carbon dioxide in the atmosphere in concomitance of other gas concentrations.

Prior art systems used in flux sites for detecting carbon dioxide and other gases required large table top size units that have significant power requirement and are unsuited for positioning on meteorological towers at remote flux sites. The inventors' apparatus, systems, and methods have use for green-house monitoring, global carbon cycle evaluation, compact NIR trace-gas spectroscopy, isotope spectroscopy, atmospheric monitoring, industrial pollution control, non-proliferation operations, cabin headspace monitoring, unmanned operations.

The apparatus, systems, and methods are susceptible to modifications and alternative forms. Specific embodiments are shown by way of example. It is to be understood that the apparatus, systems, and methods are not limited to the particular forms disclosed. The apparatus, systems, and methods cover all modifications, equivalents, and alternatives falling within the spirit and scope of the application as defined by the claims.

BRIEF DESCRIPTION OF THE DRAWINGS

The accompanying drawings, which are incorporated into and constitute a part of the specification, illustrate specific embodiments of the apparatus, systems, and methods and, together with the general description given above, and the detailed description of the specific embodiments, serve to explain the principles of the apparatus, systems, and methods.

DETAILED DESCRIPTION OF SPECIFIC EMBODIMENTS

Figure 1:
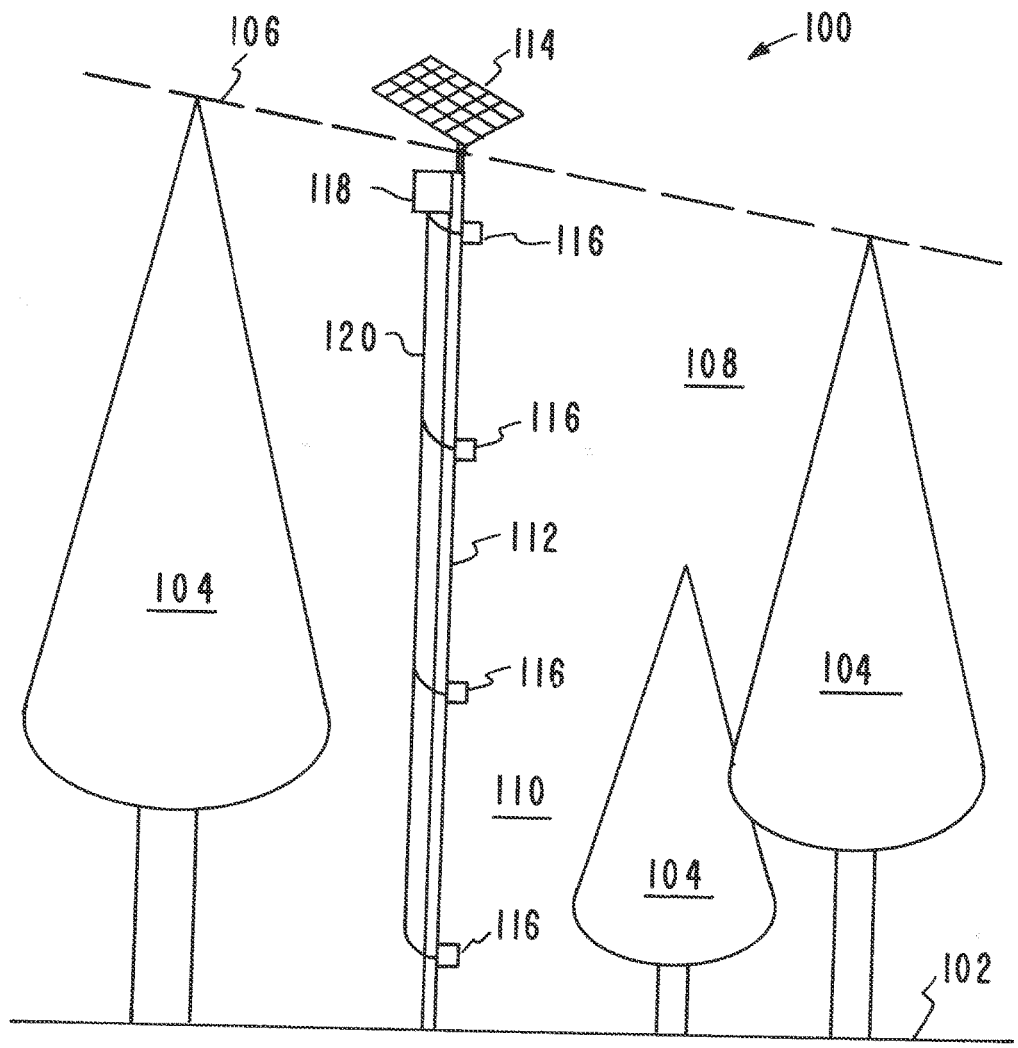
FIG. 1 illustrates one embodiment of Applicants' apparatus, systems, and methods for detecting isotopologues of $CO_2$ in the atmosphere in concomitance of $H_2O$ or $CH_4$.

Referring to the drawings, to the following detailed description, and to incorporated materials, detailed information about the apparatus, systems, and methods is provided including the description of specific embodiments. The detailed description serves to explain the principles of the apparatus, systems, and methods. The apparatus, systems, and methods are susceptible to modifications and alternative forms. The application is not limited to the particular forms disclosed. The application covers all modifications, equivalents, and alternatives falling within the spirit and scope of the apparatus, systems, and methods as defined by the claims.

The inventors' apparatus, systems, and methods provide the detection of concentrations of isotopes of carbon dioxide in the atmosphere in concomitance of other gas concentrations at a remote flux site. A meteorological tower is provided in the flux site. A solar array is positioned on the meteorological tower to provide power. A laser on the meteorological tower receives power from the solar array and produces a laser beam. A multiplicity of individual laser absorption spectroscopy gas cells positioned on the meteorological receive a sample of the atmosphere. An optical cable connects the laser to each of the individual laser absorption spectroscopy gas cells and direct the laser beam into each of the individual laser absorption spectroscopy gas cells. The individual laser absorption spectroscopy gas cells include a multiplicity of mirrors so that the laser beam makes a multiplicity of passes through the sample of the atmosphere inside of e the individual laser absorption spectroscopy gas cells. An analyzer associated with the individual laser absorption spectroscopy gas cells receives the laser beam after the laser beam has made the multiplicity of passes through the sample of the atmosphere and the analyzer detects concentrations of isotopes of carbon dioxide in the atmosphere in concomitance of other gas concentrations.

Referring now to the drawings and in particular to FIG. 1, an embodiment of the inventors' apparatus, systems, and methods for detecting isotopologues of $CO_2$ in the atmosphere in concomitance of $H_2O$ or $CH_4$ is illustrated. This embodiment is designated generally by the reference numeral 100. The flux communities operate networks and regional networks and coordinate regional and global analysis of observations from micrometeorological tower sites. The flux tower sites use eddy covariance methods to measure the exchanges of carbon dioxide ($CO_2$), water vapor, and energy between terrestrial ecosystems and the atmosphere.

The embodiment 100 is a tower site located in a forest 108. The forest 108 is made of multiple trees 104. The forest 108 has forest floor 102 and a canopy top 106. A micrometeorological tower 112 is positioned in the forest 108 and extends from the forest floor 102 to the canopy top 106. The micrometeorological tower 112 has multiple sensor units 116 positioned at different levels from the forest floor 102 to the canopy top 106. The sensor units 116 are powered by a solar array 114. A laser 118 is positioned on the tower 112 and connected to the solar array 114 for power. An optical cable 120 connects the laser 118 to each of the sensor units 116. The laser 118 produces a laser beam that is directed through the optical cable 120 to each of the sensor units 116.

Each sensor unit 116 is an apparatus for detecting isotopologues of $CO_2$ in the atmosphere in concomitance of $H_2O$ or $CH_4$, that includes a tunable diode laser absorption spectroscopy gas cell that has a laser beam, a collection system for introducing the atmosphere containing isotopologues of $CO_2$ into said tunable diode laser absorption spectroscopy gas cell, a multiplicity of mirrors in said tunable diode laser absorption spectroscopy gas cell arranged to reflect said laser beam so that said laser beam makes a multiplicity of passes through said atmosphere containing isotopologues of $CO_2$ in said tunable diode laser absorption spectroscopy gas cell, and an analyzer connected to said tunable diode laser absorption spectroscopy gas cell that detects the isotopologues of $CO_2$ in the atmosphere in concomitance of $H_2O$ or $CH_4$.

As $CO_2$ is the second most abundant greenhouse gas in the atmosphere after water vapor, predicting future climate scenarios relies strongly on the understanding and quantification of the global carbon cycle. Terrestrial vegetation accounts for the largest sink of $CO_2$ via photosynthesis, although this sink is only about 1% larger than the source of $CO_2$ emitted into the atmosphere from vegetation and soils, making it critically important to understand the tips and balances between land carbon sources and carbon sinks. While the respiration and photosynthesis respond distinctly to environmental drivers, current techniques often measure the net flux or the balance between the two and provide no specific information regarding the sensitivities of different carbon fluxes to a changing environment. Measuring the stable isotopes of carbon and oxygen in $CO_2$ indicates the effect of photosynthesis and respiration on the net ecosystem flux, but current technologies are inadequate for detecting the small changes necessary to detect these dynamic processes.

Two methods for measuring multiple gases can be used in the system 100. The first method uses a distinct cell for each target species, each with its own laser and detector. A system of multiplexing multiple lasers onto one set of fiber optics will then be connected to each cell. Output from the cell will pass through a set of filters, bandpassing the relevant spectrum for each gas to an assigned detector. Additionally, two distinct controller setups are possible with differing infrastructure requirements and sampling frequency tradeoffs. The first option involves two sources for each laser, one lock-in amplifier, and one current monitor for each detector. This option would maximize sampling frequency while also maximizing infrastructure as necessary. The second option, already tested and automated, would have fewer infrastructure requirements with only one set of controllers that are swapped among the multiple laser/detector units providing an interleaved measurement of the different gases. Reduced infrastructure comes at the cost of reduced temporal frequency of sampling. However, because the maximum sampling frequency for each spectral signature scan takes only milliseconds, achieving the 10 Hz rate currently accepted by the Ameriflux community (for gas concentrations, not isotopes) will be easily satisfied.

Figure 2:
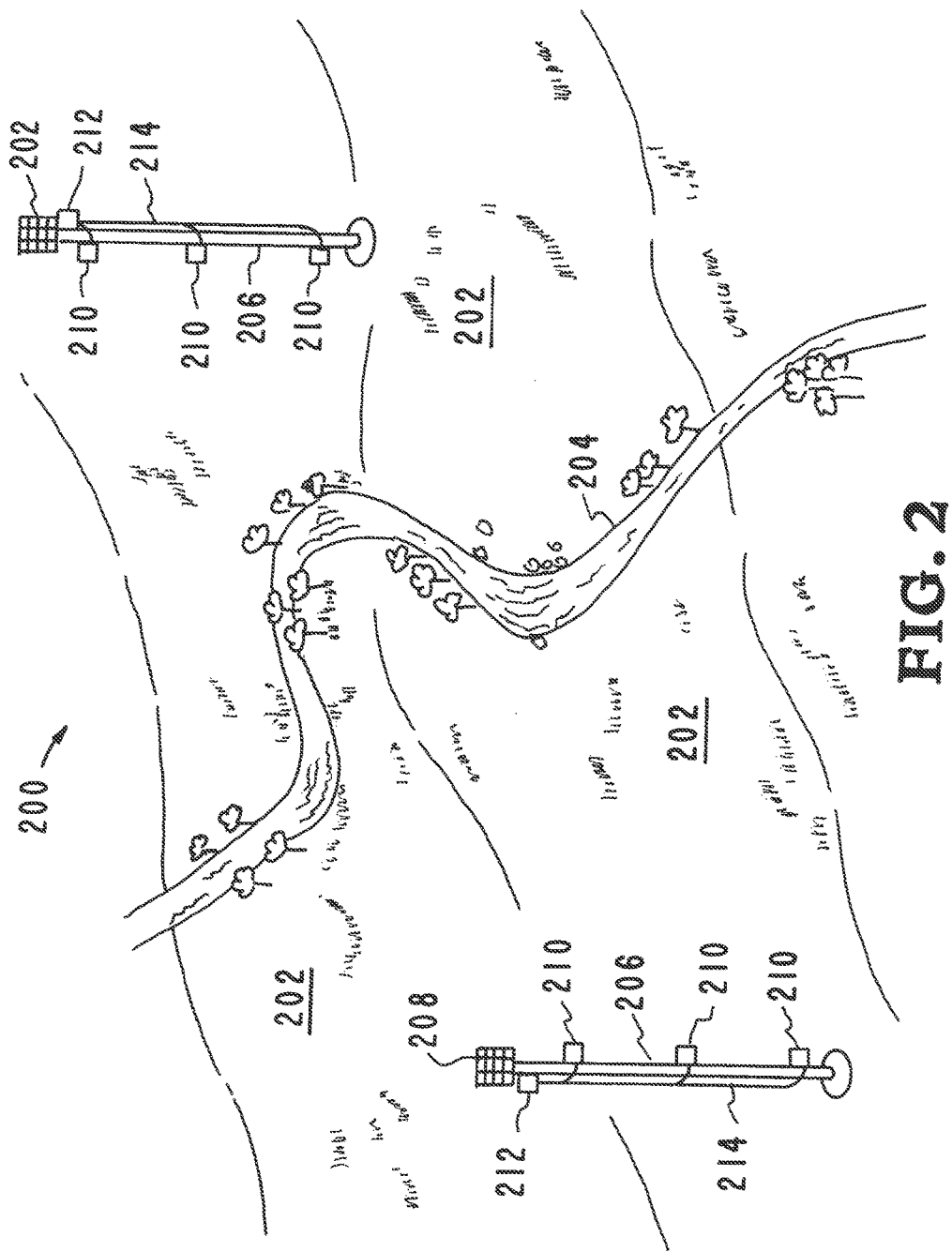
FIG. 2 illustrates another embodiment of Applicants' apparatus, systems, and methods for detecting isotopologues of $CO_2$ in the atmosphere in concomitance of $H_2O$ or $CH_4$.

Referring now to FIG. 2, another embodiment of Applicants' apparatus, systems, and methods for detecting isotopologues of $CO_2$ in the atmosphere in concomitance of $H_2O$ or $CH_4$ is illustrated. This embodiment is designated generally by the reference numeral 200. The flux communities operate networks and regional networks and coordinate regional and global analysis of observations from micrometeorological tower sites. The flux tower sites use eddy covariance methods to measure the exchanges of carbon dioxide ($CO_2$), water vapor, and energy between terrestrial ecosystems and the atmosphere.

The embodiment 200 is a tower site located in a grassy plain 202. The grassy plain 202 is made of grassy areas 202 on each side of a stream 204. The grassy plain 202 has ground level and an upper level. Micrometeorological towers 206 are positioned in the grassy plains 202 and extend from the ground level to the upper level. The micrometeorological towers 206 have multiple sensor units 210 positioned at different levels from the ground level to the upper level. The sensor units 210 are powered by a solar array 208. Lasers 212 are positioned on the towers 206 and connected to the solar array 208 for power. Optical cables 214 connect the lasers 212 to each of the sensor units 210. The lasers 212 produces a laser beam that is directed through the optical cables 214 to each of the sensor units 210.

Each sensor unit 210 is an apparatus for detecting isotopologues of $CO_2$ in the atmosphere in concomitance of $H_2O$ or $CH_4$, that includes a tunable diode laser absorption spectroscopy gas cell that has a laser beam, a collection system for introducing the atmosphere containing isotopologues of $CO_2$ into said tunable diode laser absorption spectroscopy gas cell, a multiplicity of mirrors in said tunable diode laser absorption spectroscopy gas cell arranged to reflect said laser beam so that said laser beam makes a multiplicity of passes through said atmosphere containing isotopologues of $CO_2$ in said tunable diode laser absorption spectroscopy gas cell, and an analyzer connected to said tunable diode laser absorption spectroscopy gas cell that detects the isotopologues of $CO_2$ in the atmosphere in concomitance of $H_2O$ or $CH_4$.

Figure 3:
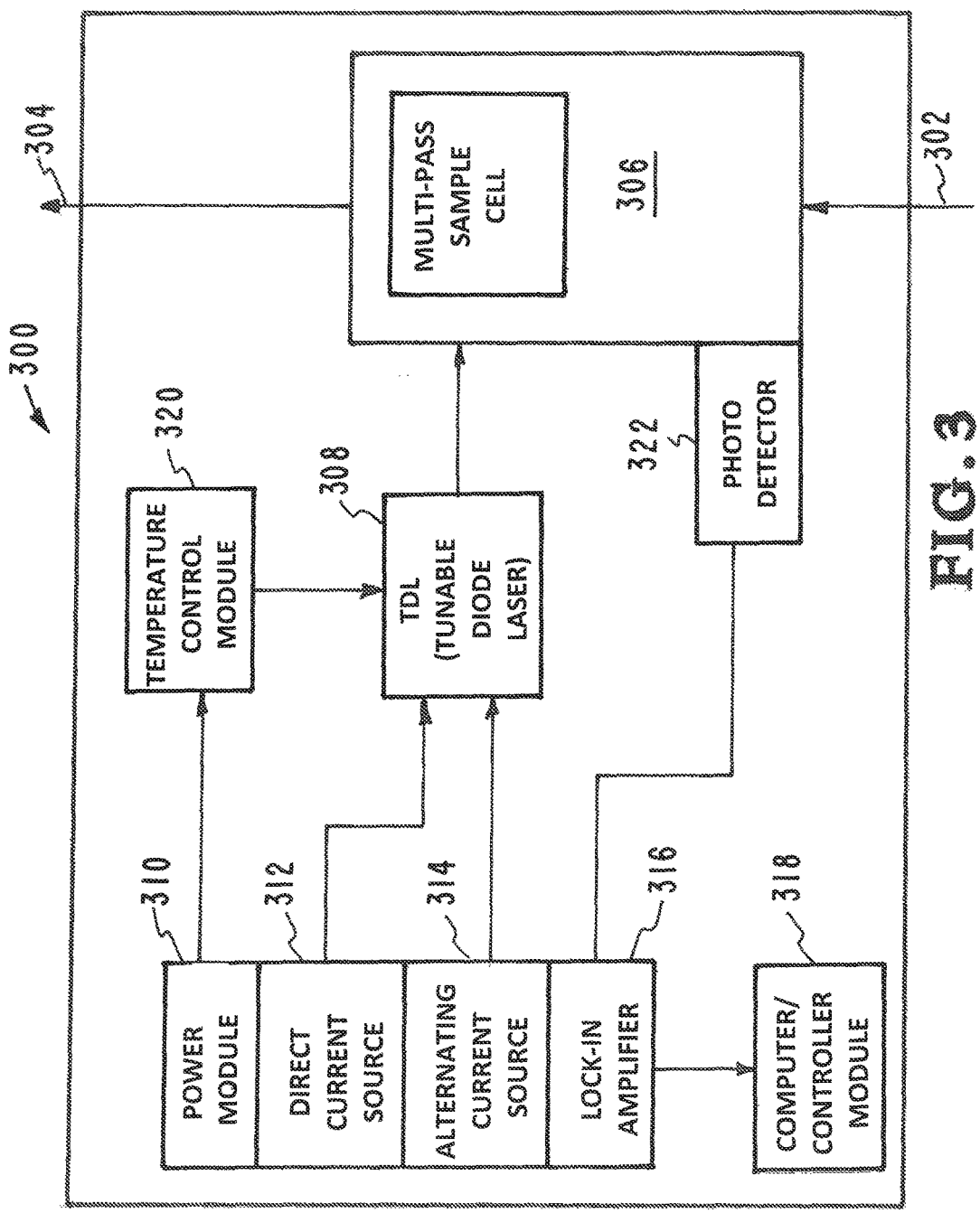
FIG. 3 illustrates a gas sensor that uses tunable diode laser absorption spectroscopy for detecting concentrations isotopes, specifically the various isotopologues of $CO_2$ in the atmosphere in concomitance of other gases concentration such $H_2O$ and $CH_4$.

Referring now to FIG. 3, a gas sensor of the inventors' apparatus, systems, and methods is illustrated. The gas sensor is designated generally by the reference numeral 300. The gas sensor 300 uses tunable diode laser absorption spectroscopy for detecting concentrations isotopes, specifically the various isotopologues of $CO_2$ in the atmosphere in concomitance of other gases concentration such $H_2O$ and $CH_4$. The gas sensor 300 includes the components listed below.

302—inlet.
304—outlet.
306—multi-pass sample cell.
308—tunable diode laser (TDL).
310—power module
312—direct current source.
314—alternating current source.
316—lock-in amplifier.
318—computer/controller module.
320—temperature control module.
322—photo detector.

The components of the gas sensor 300 having been identified and described, the operation of the gas sensor 300 will now be considered. The power module 316 is connected to the temperature control module 320, the direct current source 312, the alternating current source 314, and the lock-In amplifier 314. The temperature control module 320, the direct current source 312, and the alternating current source 314 are connected to the tunable diode laser (TDL) 308. The photo detector 322 and the outlet 304 are connected to the multi-pass sample cell 306. The photo detector 322 is connected to the lock-in amplifier 316 for signal processing. The lock-in amplifier 316 is also connected to the computer/controller module 318. In in situ operation the inlet 302 provides atmospheric air. In laboratory operations the inlet 302 provides standard air flow.

Figure 4:
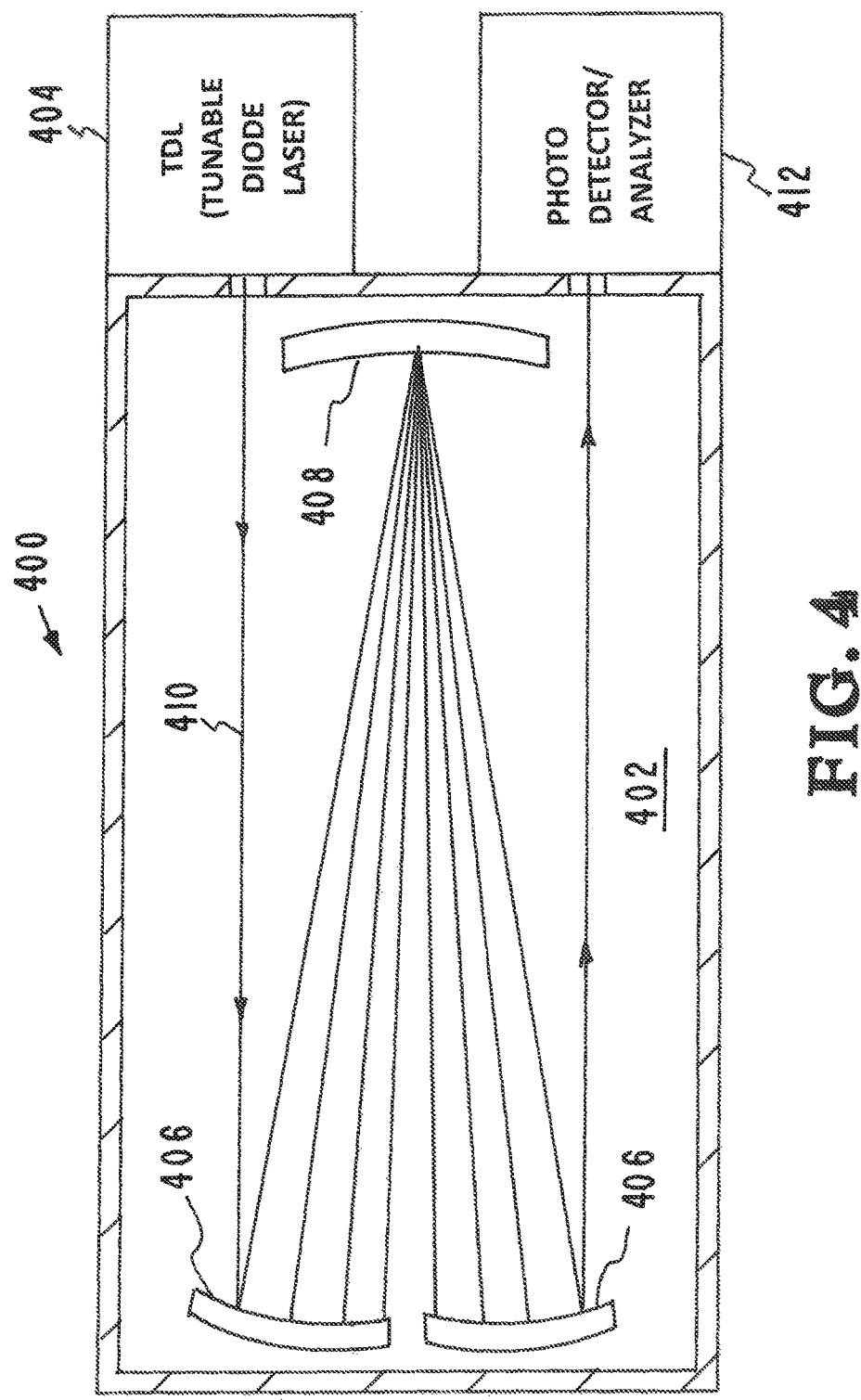
FIG. 4 is an illustration of the gas cell of the inventors' apparatus, systems, and method for detecting isotopologues of $CO_2$ in the atmosphere in concomitance of $H_2O$ or $CH_4$ illustrated in FIGS. 1 and 2.

A minicell is one of the components of the gas sensor system illustrated in FIGS. 1, 2, and 3. Referring to FIG. 4, a first example of one embodiment of a minicell is illustrated. The minicell is designated generally by the reference numeral 400. This example of a minicell 400 is based upon the minicell shown in U.S. Pat. No. 9,234,794 issued Jan. 12, 2016 to Applicants in this application; Tiziana C. Bond and Mihall Bora and others.

The minicell 400 is a multipass White cell that has a total of 28 passes for an effective length of 1.6 m, in a footprint of 110 mm×60 mm×40 mm (4.33"×2.36"×1.57"). The minicell 400 includes an inlet and an outlet for introducing and removing the gas of interest into the interior 402 of the minicell 400. A laser source 404 directs a laser beam 410 into the minicell 400. The laser source 404 can be the optical fiber illustrated in FIGS. 1 and 2.

A first set of mirrors 406 and an opposing mirror 408 are positioned to reflect the laser beam 410 so that it makes multipasses through the interior 402 of the minicell 400. The mirrors 406 and the mirror 404 are accurately positioned so that the reflected laser beam 410 makes twenty eight (28) passes through the interior 402 of the minicell 400 and through the gas of interest within the minicell 400. On the last pass the laser beam 410 exits the mincell 400 into the photo detector 412.

The structural details of the minicell 400 having been described the operation of the operation of the minicell apparatus and system 400 for gas spectroscopy of a gas of interest will be considered. The multi-pass cell 400 is composed of the sets of mirrors 406 and 408. The two mirrors 406 on one side have their inclination offset from each other and help steer the beam 410 inside the cavity 402. The opposing mirror 408 has two notches cut in to allow the entrance and exit beams inside the cell. Applicants control the intensity of the laser beam right at the surface of the mirrors. Because the output of the laser diode is divergent with an opening of about 30 degrees the beam steering mirrors are filled completely. The optical focal length of the mirrors is chosen as a 1:1 relay imaging system, such that the beams are focused on the entrance/exit mirror to avoid chopping the beam at the edges and hence losing signal, while also allowing a higher number of passes.

Figure 5:
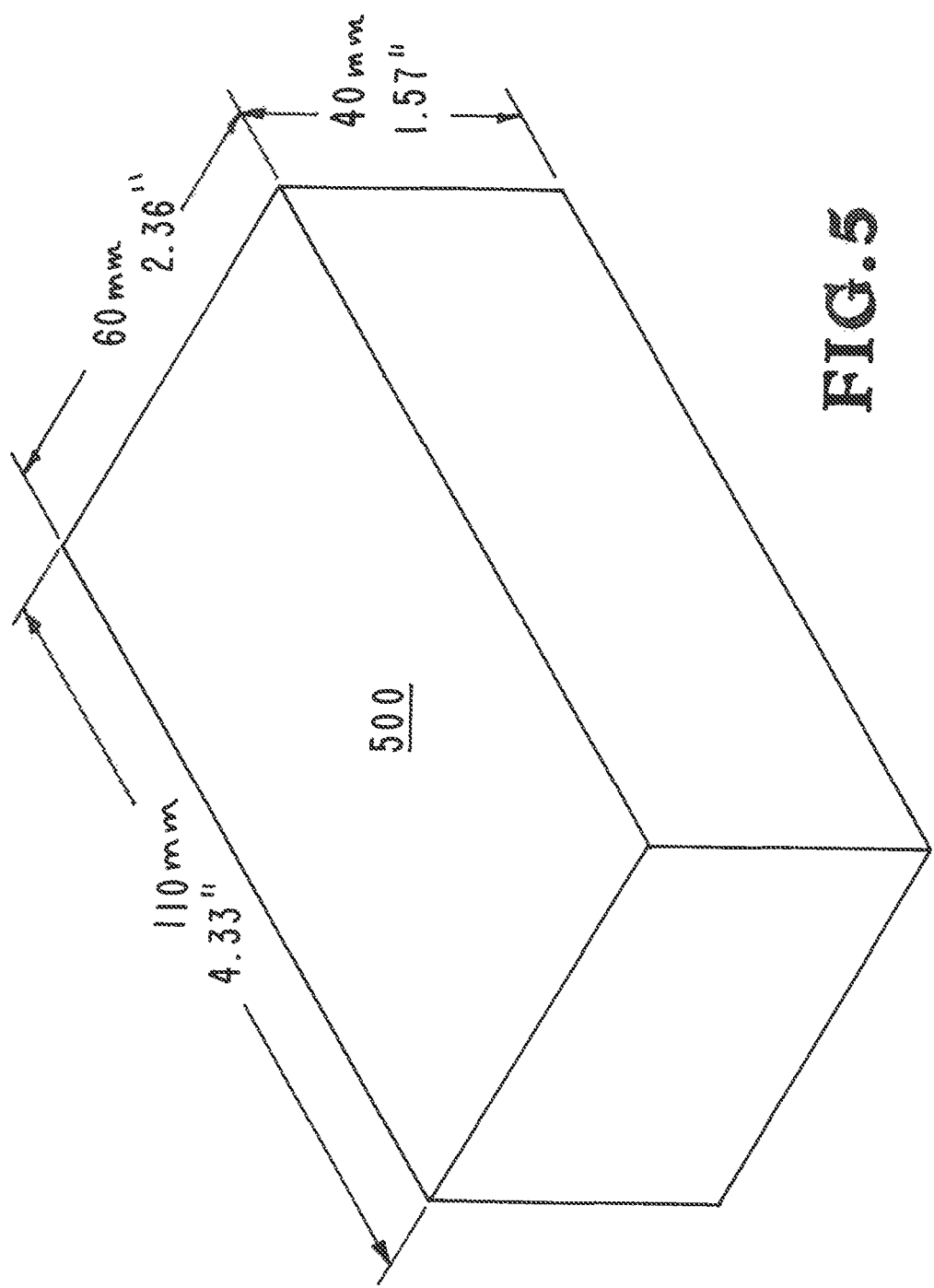
FIG. 5 illustrates one embodiment of the inventors' miniaturized gas cell with a small footprint.

Referring now to FIG. 5, the inventors have developed a miniaturized gas cell with a small footprint. The minicell is designated generally by the reference numeral 500. The minicell 500 is a multipass White cell that has a footprint of 110 mm×60 mm×40 mm (4.33"×2.36"×1.57"). The minicell 500 contains a multiplicity of mirrors positioned so that said laser beam makes a multiplicity of passes through the sample of the atmosphere inside of the cell 500. A first concave mirror, a second concave mirror, and a third concave mirror are positioned inside of the cell. The first concave mirror is opposed to the second concave mirror and the third concave mirror so that the laser beam makes twenty eight passes through the sample of the atmosphere.

Although the description above contains many details and specifics, these should not be construed as limiting the scope of the application but as merely providing illustrations of some of the presently preferred embodiments of the apparatus, systems, and methods. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present application fully encompasses other embodiments which may become obvious to those skilled in the art. In the claims, reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present apparatus, systems, and methods, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

While the apparatus, systems, and methods may be susceptible to various modifications and alternative forms, specific embodiments have been shown by way of example in the drawings and have been described in detail herein. However, it should be understood that the application is not intended to be limited to the particular forms disclosed. Rather, the application is to cover all modifications, equivalents, and alternatives falling within the spirit and scope of the application as defined by the following appended claims.

The claims are:

1. An apparatus for use in a flux site in a grassy plain having a ground level and an upper level and different levels located between the ground level and the upper level wherein the apparatus is used for detecting concentrations of isotopes of carbon dioxide in the atmosphere in concomitance of other gas concentrations, comprising:
   a meteorological tower in the flux site in a grassy plain, wherein said meteorological tower extends from the ground level to the upper level;
   a solar array connected to said meteorological tower and positioned above said upper level, wherein said solar array produces power;
   a laser in the flux site positioned on and connected to said meteorological tower, wherein said laser receives said power from said solar array and wherein said laser produces a laser beam;
   a multiplicity of individual laser absorption spectroscopy gas cells positioned on and connected to said meteorological tower,
   wherein each of said individual laser absorption spectroscopy gas cells are positioned on said meteorological tower at the different levels located between the ground level and the upper level,
   wherein said multiplicity of individual laser absorption spectroscopy gas cells receive said power from said solar array, and
   wherein said multiplicity of individual laser absorption spectroscopy gas cells receive a sample of the atmosphere;
   an optical cable connecting said laser to each of said individual laser absorption spectroscopy gas cells, wherein said optical cable directs said laser beam into each of said individual laser absorption spectroscopy gas cells, wherein each of said individual laser absorption spectroscopy gas cells includes a multiplicity of mirrors positioned inside of each of said individual laser absorption spectroscopy gas cells so that said laser beam makes a multiplicity of passes through said sample of the atmosphere inside of each of said individual laser absorption spectroscopy gas cells, wherein each of said individual laser absorption spectroscopy gas cells includes a first concave mirror, a second concave mirror, and a third concave mirror positioned so that said first concave mirror is opposed to said second concave mirror and is opposed to said third concave mirror to cause said laser beam to make twenty eight passes through said sample of the atmosphere; and an analyzer associated with each said individual laser absorption spectroscopy gas cells wherein said analyzer receives said laser beam after said laser beam has made said multiplicity of passes through said sample of the atmosphere and said analyzer detects concentrations of isotopes of carbon dioxide in the atmosphere in concomitance of other gas concentrations.

2. The apparatus for use in a flux site for detecting concentrations of isotopes of carbon dioxide in the atmosphere in concomitance of other gas concentrations of claim 1 wherein said individual laser absorption spectroscopy gas cells are tunable diode laser absorption spectroscopy gas cells.

3. An apparatus for detecting isotopologues of carbon dioxide in the atmosphere in concomitance of water or methane in a flux site in a forest having a forest floor and a canopy top and different levels located between the forest floor and the canopy top, comprising:

a meteorological tower in the flux site in the forest wherein said meteorological tower extends from the forest floor to the canopy top;

a solar array connected to said meteorological tower and positioned above said canopy top, wherein said solar array produces power;

a laser in the flux site positioned on and connected to said meteorological tower, wherein said laser receives said power from said solar array and wherein said laser produces a laser beam;

a multiplicity of individual laser absorption spectroscopy gas cells connected to said meteorological tower, wherein each of said individual laser absorption spectroscopy gas cells are positioned on said meteorological tower at the different levels located between the forest floor and the canopy top, wherein each of said individual laser absorption spectroscopy gas cells receives said power from said solar array; and wherein each of said individual laser absorption spectroscopy gas cells receives a sample of the atmosphere;

an optical cable connected to said laser and connected to each of said individual laser absorption spectroscopy gas cells;

wherein said optical cable directs said laser beam into each of said individual laser absorption spectroscopy gas cells, wherein each of said individual laser absorption spectroscopy gas cells includes a multiplicity of mirrors positioned inside of each of said individual laser absorption spectroscopy gas cells so that said laser beam makes a multiplicity of passes through said sample of the atmosphere, wherein each of said individual laser absorption spectroscopy gas cells includes a first concave mirror, a second concave mirror, and a third concave mirror positioned so that said first concave mirror is opposed to said second concave mirror and is opposed to said third concave mirror to cause said laser beam to make twenty eight passes through said sample of the atmosphere; and an analyzer associated with each said individual laser absorption spectroscopy gas cells wherein said analyzer receives said laser beam after said laser beam has made said multiplicity of passes through said sample of the atmosphere and said analyzer detects the isotopologues of carbon dioxide in the atmosphere in concomitance of water or methane.

4. The apparatus for detecting isotopologues of carbon dioxide in the atmosphere in concomitance of water or methane of claim 3 wherein said individual laser absorption spectroscopy gas cells are tunable diode laser absorption spectroscopy gas cells.

5. The apparatus for detecting isotopologues of carbon dioxide in the atmosphere in concomitance of water or methane of claim 3 wherein said multiplicity of mirrors positioned inside of each of said individual laser absorption spectroscopy gas cells so that said laser beam makes a multiplicity of passes through said sample of the atmosphere comprises three individual mirrors positioned inside of each of said individual laser absorption spectroscopy gas cells so that said laser beam makes a multiplicity of passes through said sample of the atmosphere.

6. A method of detecting isotopologues of carbon dioxide in the atmosphere in concomitance of water or methane for use in a flux site in a forest having a forest floor and a canopy top and different levels located between the forest floor and the canopy top, comprising the steps of:

providing a meteorological tower in the flux site in the forest wherein said meteorological tower extends from the forest floor to the canopy top, positioning a solar array connected to said meteorological tower and positioned above said canopy top wherein said solar array produces power, positioning a laser on said meteorological tower that receives said power from said solar array wherein said laser produces a laser beam, providing and optical cable connected to said laser that transmits said laser beam;

positioning a multiplicity of individual laser absorption spectroscopy gas cells on said meteorological tower, wherein each of said individual laser absorption spectroscopy gas cells are positioned on said meteorological tower at the different levels located between the forest floor and the canopy top, wherein each of said individual laser absorption spectroscopy gas cells receives said power from said solar array, and wherein each of said individual laser absorption spectroscopy gas cells receives a sample of the atmosphere;

connecting an optical cable from said laser to each of said individual laser absorption spectroscopy gas cells, wherein said optical cable directs said laser beam into each of said individual laser absorption spectroscopy gas cells, wherein each of said individual laser absorption spectroscopy gas cells includes a multiplicity of mirrors positioned inside of each of said individual laser absorption spectroscopy gas cells so that said laser beam makes a multiplicity of passes through said sample of the atmosphere, wherein each of said individual laser absorption spectroscopy gas cells includes a first concave mirror, a second concave mirror, and a third concave mirror positioned so that said first concave mirror is opposed to said second concave mirror and is opposed to said third concave mirror to cause said laser beam to make twenty eight passes through said sample of the atmosphere;

directing said laser beam to an analyzer after said laser beam has made said multiplicity of passes through said sample of the atmosphere, and using said analyzer to analyze for detecting concentrations of isotopes of carbon dioxide in the atmosphere in concomitance of other gas concentrations.

* * * * *